United States Patent [19]
Maloney et al.

[11] Patent Number: 5,873,832
[45] Date of Patent: Feb. 23, 1999

[54] METHOD AND APPARATUS FOR MEASURING PROPERTIES OF THE EYE USING A VIRTUAL IMAGE

[75] Inventors: Robert K. Maloney, Pacific Palisades, Calif.; Jeffrey L. Stewart, Greenwich, Conn.

[73] Assignee: Xeyex Corporation, Greenwich, Conn.

[21] Appl. No.: 695,616

[22] Filed: Aug. 12, 1996

[51] Int. Cl.$^6$ ........................................... A61B 6/00
[52] U.S. Cl. ................ 600/473; 600/476; 351/207; 351/212
[58] Field of Search ................ 606/4–6, 10–12; 351/205, 206, 211, 207, 212, 215; 128/664, 665, 745

[56] References Cited

U.S. PATENT DOCUMENTS

| | | |
|---|---|---|
| 2,765,702 | 10/1956 | Sachtleben . |
| 4,019,813 | 4/1977 | Cornsweet et al. . |
| 4,093,360 | 6/1978 | Mohrman et al. . |
| 4,315,672 | 2/1982 | Müller et al. . |
| 4,456,348 | 6/1984 | Schulz et al. . |
| 4,761,071 | 8/1988 | Baron . |
| 4,796,989 | 1/1989 | Fukuma et al. . |
| 4,874,236 | 10/1989 | Abraham . |
| 4,878,750 | 11/1989 | Sekiguchi . |
| 4,929,076 | 5/1990 | Masuda et al. . |
| 5,033,841 | 7/1991 | Nishio et al. . |
| 5,062,702 | 11/1991 | Bille ........................................... 351/212 |
| 5,116,114 | 5/1992 | Nakamura et al. . |
| 5,131,739 | 7/1992 | Katsuragi . |
| 5,258,791 | 11/1993 | Penney et al. ........................... 351/211 |
| 5,307,096 | 4/1994 | Baroth et al. . |
| 5,325,135 | 6/1994 | Nakamura et al. . |
| 5,414,478 | 5/1995 | van Gelderen . |
| 5,418,582 | 5/1995 | van Saarloos . |
| 5,585,872 | 12/1996 | Kohayakawa ........................... 351/212 |
| 5,592,246 | 1/1997 | Kuhn et al. ............................. 351/212 |

Primary Examiner—Max Hindenburg
Assistant Examiner—Bryan K. Yarnell
Attorney, Agent, or Firm—J. De La Rosa

[57] ABSTRACT

A technique for evaluating the topography of a cornea, which utilizes a virtual image of a keratoscope pattern. The topography system includes a structured light source to create the keratoscope pattern or another diagnostic pattern, an optical assembly to focus the created pattern upon the cornea, and for capturing the image reflected off the patient's eye and directing the reflected image towards an imaging system for processing. Light emitted by the light source is preferably not in the visible range, to minimize discomfort to the patient. Since the topography is evaluated with a projected virtual image, there is no nose or brow shadow, thereby alowing better corneal coverage. The optical system includes an aperture stop which is preferably conjugate with a point behind the corneal surface approximating the center of a normal cornea. Thus, wide angle capture is achieved as reflected rays reaching the imaging system appear as if they originated at the center of the cornea. A pupil detection mechanism is disclosed which is performed independently of the diagnostic pattern illumination, thereby facilitating pupil detection. In an alternate embodiment, the diagnostic pattern is generated using a variable light pattern generator, which provides flexibility in selecting target images to achieve various diagnostic abilities. The disclosed topography system can be reconfigured to serve as a visual field measuring device, or a perimeter.

21 Claims, 10 Drawing Sheets

METHOD AND APPARATUS FOR MEASURING PROPERTIES OF THE EYE USING A VIRTUAL IMAGE

FIELD OF THE INVENTION

The present invention relates to a device for evaluating the curvature or shape of the cornea of the eye, and more particularly, to a corneal measurement device that assists with pre-operative or post-operative measurements of the cornea, with contact lens fitting and with the diagnosis of diseases of the cornea.

BACKGROUND OF THE INVENTION

The cornea, being the front surface of the eye, provides its major refracting surface and is important to quality vision. Recently, a number of corneal surgical techniques have been developed for correcting visual deficiencies, such as near-sightedness, far-sightedness and astigmatism. In order to assist with such surgical techniques, a number of devices have been proposed or developed to evaluate the topography, i.e., the shape or curvature, of the cornea. In addition, such corneal topography techniques are useful for fitting contact lenses and for the diagnosis and management of corneal pathologic conditions, such as keratoconus and other ectasias. For example, prior to performing a corneal surgical technique to correct a refractive error, the patient is preferably screened using a corneal topography device to rule out the possibility of subclinical keratoconus.

Corneal topography is typically measured using a series of concentric lighted rings, known as a keratoscope pattern 5, shown in FIG. 1. In one typical embodiment, shown in FIG. 2, the keratoscope pattern 5 is created by a keratoscope target 10, consisting of illuminated concentric rings which emit light rays which are projected onto the cornea of the patient's eye 15. Light rays 12,20 are reflected off the patient's cornea 15, and a portion of the light 20 is captured by an objective lens 25 and focused onto an imaging system 30, such as a video camera. A computer 35 is utilized to compare the image captured on imaging system 30 with a stored reference pattern, or other known information, to identify any distortions in the captured image and thus calculate any deformations in the patient's cornea.

While conventional corneal topography devices have achieved significant success, such devices suffer from a number of limitations, which, if overcome, could significantly enhance their accuracy and utility. In particular, earlier designs for topography devices have incorporated large keratoscope targets, causing the overall size of the prior devices to be quite large. In an operating room or a doctor's office, however, where space is at a premium, it is desirable to minimize the overall size of the topography device.

In addition, commercially available topography devices, such as the design illustrated in FIG. 2, typically measure the topography of only a relatively small area of the cornea. For example, in the design shown in FIG. 2, the light beam is emitted from a large, flat, backlit keratoscope target 10 and is then reflected off the cornea 15. Thereafter, a portion of the light 20 reflected off the cornea 15 is focused by a small objective lens 25 at the center of the keratoscope target 10 onto the imaging system 30, such as a CCD chip. Additional light rays 12 reflected from the peripheral portions of the cornea 15, however, are not captured by the objective lens 25 and are therefore not imaged onto the imaging system 30. Therefore, such prior art devices are unable to measure the peripheral cornea.

To overcome this problem, prior devices have attempted to capture the light rays reflected from the peripheral portions of the cornea 15 by designing a keratoscope target 10' in the shape of a cylinder or cone, as shown in FIG. 3, encompassing the peripheral cornea. In this manner, light rays emitted by the cylindrical or conical keratoscope target 10' will form a pattern 5 of illuminated rings which will be reflected off the cornea 15. The reflected light rays, including light rays reflected off the peripheral portions of the cornea 15, will be captured by the objective lens 25 and imaged onto the imaging system 30. To be effective, however, the cylindrical or conical keratoscope target 10' must be positioned very close to the eye, and thereby tends to impinge on the patient's brow and nose. In addition to being potentially uncomfortable and potentially contributing to the spread of disease, the close approach of the keratoscope target 10' makes the design very error-prone, as a slight error in alignment or focusing causes a large percentage change in the position of the keratoscope rings relative to the eye.

In addition, current systems tend to provide poor pupil detection and do not accurately measure non-rotationally symmetric corneas, such as those with astigmatism. The location of the pupil is particularly important in planning surgical procedures for correcting visual deficiencies. In current systems, pupils are typically detected by deciphering the border of the pupil from the image of the keratoscope rings. This is particularly difficult with conventional designs, however, as the intensity transition from the black pupil to a dark iris is minimal compared to the intensity transition from a bright keratoscope ring image to a dark interring spacing. As a result, the pupil detection algorithms in current systems often fail.

Furthermore, current systems have difficulty detecting the edges of the keratoscope rings and difficulty separating ring images from background iris detail. Conventional corneal topography systems image the iris along with the keratoscope rings. Particularly in patients having light-colored irises, however, the bright reflection from iris detail obscures the rings, thereby making detection of ring edges difficult. Finally, conventional devices utilize high intensity visible light to illuminate the keratoscope target and therefore cause discomfort to the patient. The high intensity light is required because relatively little light is actually reflected from the cornea and captured by the measuring devices.

As is apparent from the above discussion, a need exists for a more compact corneal topography device. Another need exists for a topography system that allows a large area of corneal coverage without the focusing problems and invasive approach of previous designs. A further need exists for a system incorporating improved pupil detection by using an image that does not include the keratoscope rings. Yet another need exists for a topography device providing improved separation of the corneal reflection of the keratoscope pattern from the iris detail. A further need exists for a topography system utilizing light levels that are not unpleasant for the subject undergoing measurement. An additional need exists for a topography device that permits accurate measurement of non-rotationally symmetric corneas, such as those with astigmatism.

SUMMARY OF THE INVENTION

Generally, according to aspects of the present invention, a method and apparatus for measuring the topography of the cornea are provided. The method and apparatus utilize a virtual image of a keratoscope pattern or another diagnostic pattern, which is projected at a desired distance in front of the patient's eye. Since the topography is evaluated with a virtual image, there is no nose or brow shadow, allowing better coverage of the cornea and providing a design which is relatively insensitive to focusing errors.

The disclosed topography system includes a structured light source, preferably consisting of an illumination source and a beam modulating system, to create the keratoscope pattern or another desired diagnostic pattern. In order to minimize discomfort to the patient, light emitted by the illumination source is preferably not in the visible range. In addition, the illumination source is preferably monochromatic.

In accordance with an aspect of the present invention, the beam modulating system may be embodied as a photographic slide film consisting of opaque markings on a transparent background, or a variable light pattern generator, such as an array of liquid crystal pixels, or an array of light emitting diodes. In this manner, the beam modulating system can provide flexibility in selecting pattern images to achieve various diagnostic abilities.

An optical assembly focuses the created pattern upon the cornea, and thereafter captures the image reflected off the patient's eye and directs the reflected image towards an imaging system, such as a CCD chip, for processing. According to a feature of the invention, the optical assembly preferably includes means for preventing scattered light reflected from the patient's iris from being imaged by the CCD chip. In one embodiment, a pair of polarizing filters having the same polarization attenuate the scattered light reflected from the patient's iris, thereby permitting a clean image of the keratoscope pattern, as reflected off the patient's cornea, on the CCD camera.

According to a further feature of the invention, the optical system achieves wide angle capture by including an aperture stop which is preferably conjugate with a point behind the corneal surface approximating the center of curvature of a normal cornea. Thus, reflected rays reaching the imaging system appear as if they originated at the center of curvature of the cornea.

The corneal topography device preferably includes a centration illumination source and a focusing laser which are utilized to center and focus the corneal topography system relative to the patient's cornea. During the centration and focusing operation, the structured light source used to generate the diagnostic pattern is preferably not illuminated. Thus, pupil detection is facilitated, since the pupil boundaries are not obscured by one or more rings of the keratoscope pattern.

In accordance with a further aspect of the invention, a method of calibrating the corneal topography device is disclosed. The method comprises the steps of: positioning a calibration sphere approximating the size of a cornea at a desired focal point; illuminating the calibration sphere with a diagnostic pattern; creating a first image on an imaging system of a reflection of the diagnostic pattern off the sphere; positioning a cursor on the imaging system at approximately the center of the first image; creating a second image on the imaging system of a reflection of a centration illumination source off the sphere; adjusting the position of the centration illumination source so that the second image is approximately centered around the previously positioned cursor; and storing the first image as a reference image for calculating topographical information about an unknown cornea.

Yet another aspect of the invention allows the disclosed topography system to be reconfigured as a perimeter to evaluate a patient's field of vision. When configured as a perimeter, the structured light source is preferably embodied as a backlit liquid crystal array, a cathode ray tube or an array of light emitting diodes. To measure the patient's visual field, the patient observes a virtual image of the pattern produced by the structured light source, which is projected at a distance in front of the patients eye. In addition, an infrared laser illuminates the patient's pupil with an infrared beam. A reflection of the infrared beam scattered off the patient's iris is imaged on the CCD chip. According to a further feature of the invention, the optical system includes means for attenuating light which is reflected off the patient's cornea during the visual field measurement, such as a pair of perpendicular polarizers positioned in the optical path. The system monitors fixation by tracking the movement of the pupil, using the scattered infrared image. When the center of the pupil moves beyond a predefined threshold, an alarm indicates when fixation is lost.

A more complete understanding of the present invention, as well as further features and advantages of the invention, will be obtained by reference to the detailed description and drawings.

DETAILED DESCRIPTION

Figure 1:
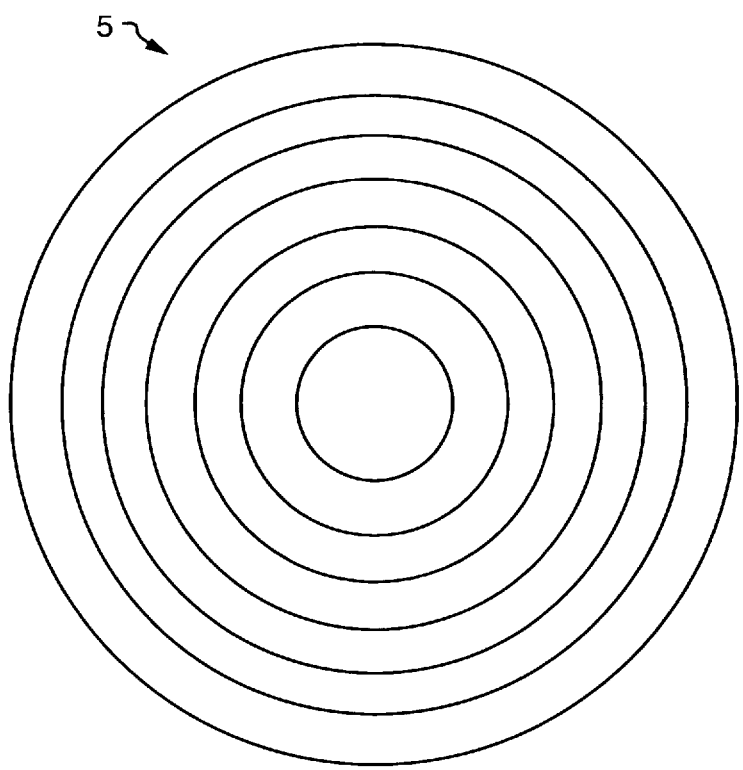
FIG. 1 is a diagram illustrating a keratoscope pattern of the prior art.
Figure 4:
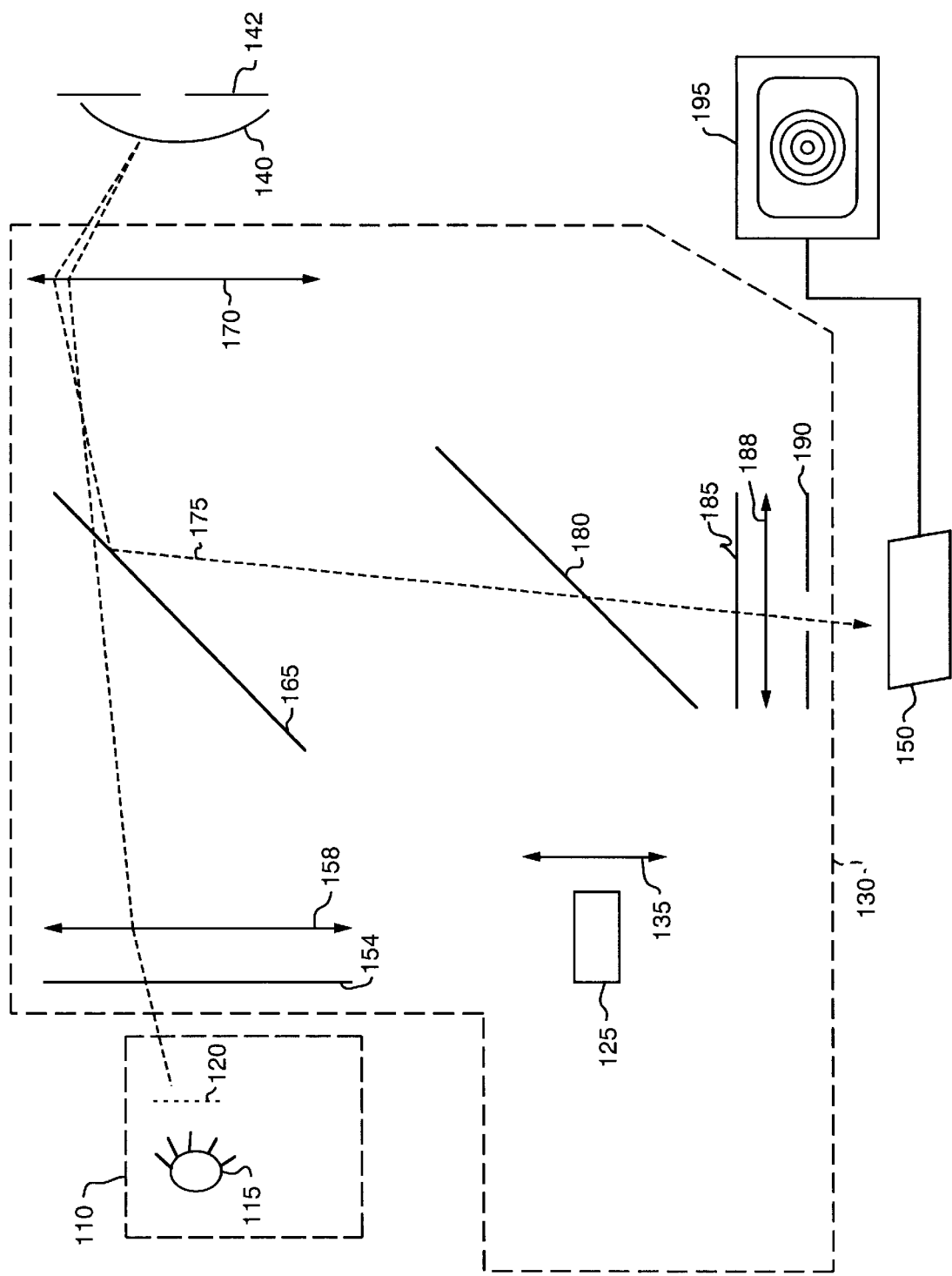
FIG. 4 is a block diagram of a corneal topography device incorporating features of the present invention.

As shown in FIG. 4, a corneal topography device according to the present invention includes a structured light source 110, for creating a diagnostic pattern, such as the keratoscope pattern 5 (FIG. 1), and an optical assembly 130 for focusing the created pattern 5 upon the cornea 140 of a patient's eye and for capturing the pattern reflected off the patient's eye and directing the reflected pattern towards an imaging system 150, such as a CCD chip, for further processing. The structured light source 110 preferably consists of an illumination source 115 and a beam modulating system 120 for creating the keratoscope pattern 5, as illustrated in FIG. 1, or an alternate pattern as discussed below. In one embodiment, the structured light source 110 includes a diffuser to spread out the light.

According to one feature of the invention, light emitted from the illumination source 115 is preferably not in the visible range, thereby minimizing the discomfort to the patient resulting from the high intensity source. In one embodiment, the beam modulating system 120 for creating the keratoscope pattern 5 is embodied as photographic slide film consisting of opaque markings on a transparent background.

As shown in FIG. 4, the optical assembly 130 preferably includes, in sequence, a polarizing filter 154, a focusing lens 158, for capturing and directing the polarized light upon a beam splitter 165 and an objective lens 170, which focuses the pattern 5 upon the cornea 140. In addition, the light 175 reflected from the cornea 140 is captured by objective lens 170 and is then reflected by beam splitter 165 towards a second beam splitter 180. The light passes through beam splitter 180, in a known manner, and through polarizing filter 185, which is oriented parallel to polarizing filter 154. Thereafter, the light passes through a focusing lens 188, which serves to direct the reflected pattern through an aperture stop 190, such as an adjustable round hole or an iris, and onto the CCD chip 150. The CCD chip 150 transmits the captured image to a personal computer 195, or another processor, where the image of the reflected pattern is displayed on a computer screen for further evaluation by an operator.

According to a further feature of the invention, the polarizing filter 185, having the same polarization as polarizing filter 154, serves to prevent scattered light reflecting from the patient's iris 142 from being imaged on the CCD chip 150. In this manner, scattered light reflected from the patient's iris 142 is attenuated, permitting a clean image of the keratoscope pattern, as reflected off the cornea 140, on the CCD camera, without noise and background detail from the patient's iris 142, thereby simplifying image processing.

Figure 7:
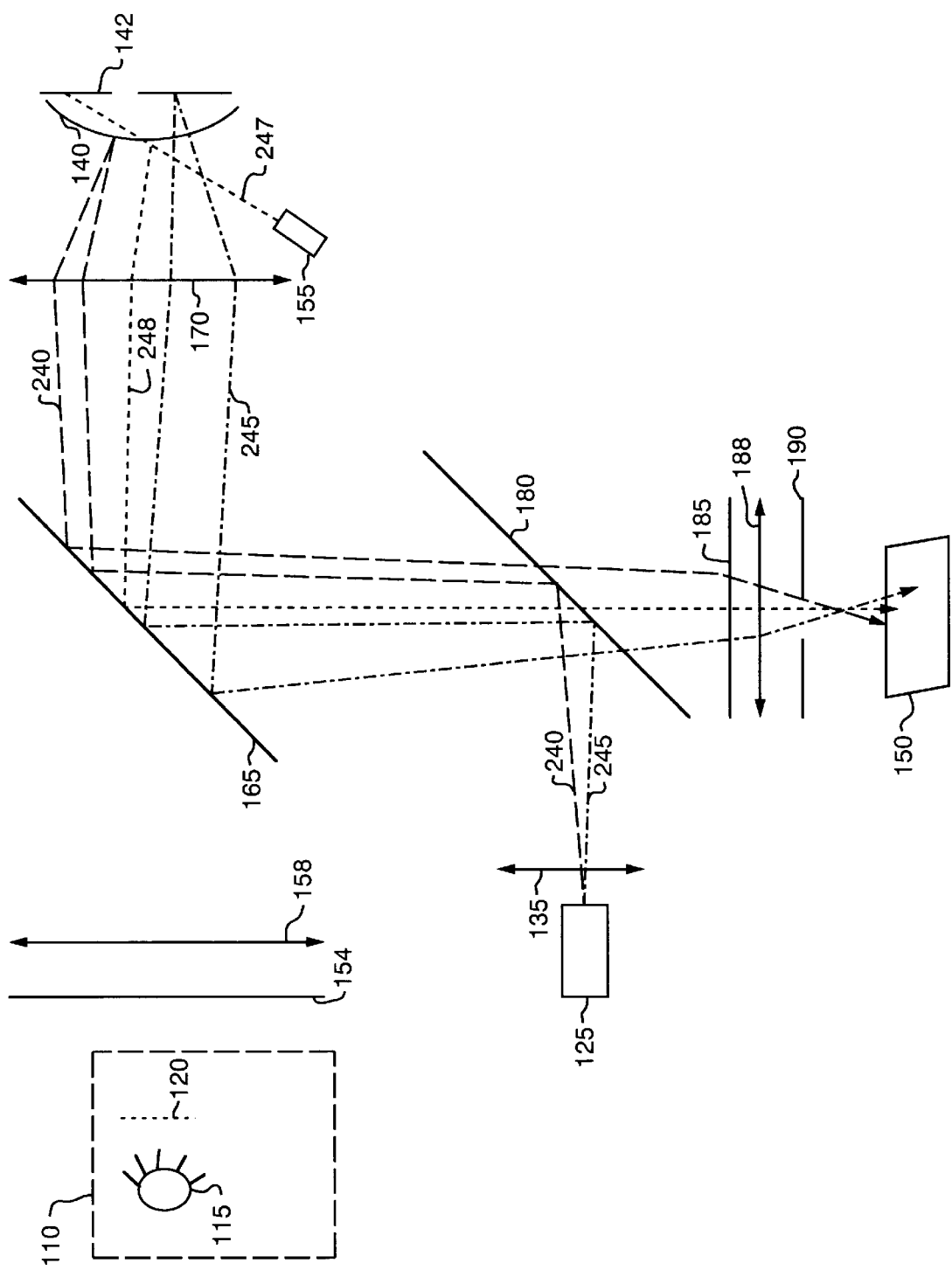
FIG. 7 illustrates the corneal topography device of FIG. 4 in operation during focusing and centration.

In addition, the corneal topography device includes a centration illumination source 125 and a collimating lens 135, and a focusing laser 155, discussed further below in conjunction with FIG. 7, which are utilized during a centration and focusing process to center and focus the corneal topography system relative to the patient's cornea 140. In a further embodiment, discussed below in conjunction with FIG. 10, the topography device may be configured as a perimeter to evaluate the patient's field of vision. When configured as a perimeter, the centration illumination source 125 preferably emits light in the infrared range.

Figure 5:
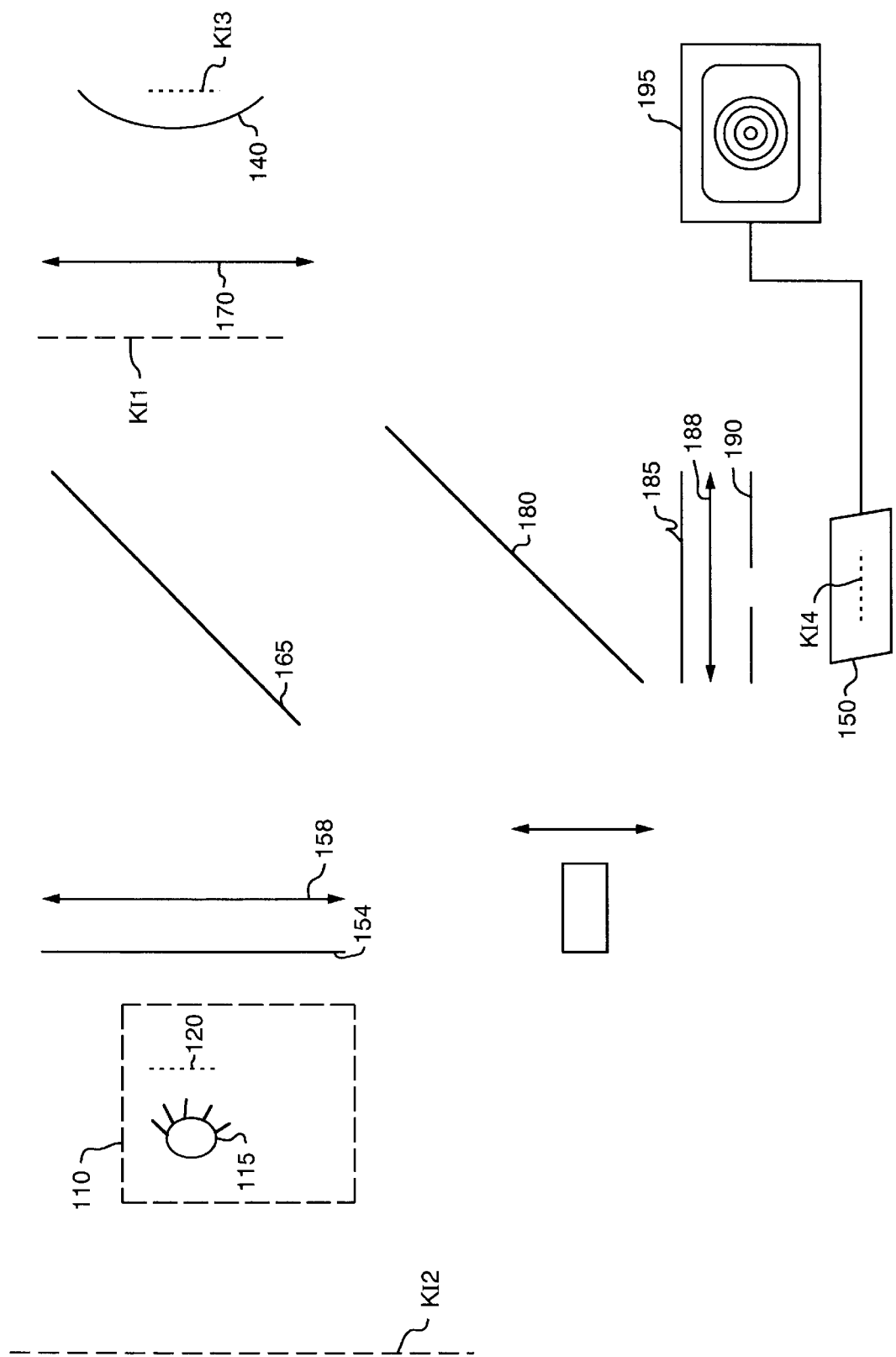
FIG. 5 illustrates the location of real and virtual images of the keratoscope pattern in the embodiment of FIG. 4.

As the light beam passes from the beam modulating system 120 through the various elements of the optical system 130 to the CCD chip 150, several images, including real images and virtual images, of the keratoscope pattern are created, as illustrated in FIG. 5. Image KI1 is a real image of the keratoscope pattern 5 created by focusing lens 158 and lying inside the focal point of objective lens 170. In a real image, all the light from a point on the pattern passing through the optical system, actually passes close to or through a point on the image. In other words, because KI1 is a real image, the keratoscope pattern 5 could actually be seen on a piece of paper, if a piece of paper were inserted into the optical assembly at the location of KI1.

In addition, objective lens 170 projects image KI1 to create a virtual image KI2 of the keratoscope pattern 5, preferably lying approximately 0.3 meters in front of the patient's eye and being approximately 0.4 meters in diameter. In a virtual image, rays of light only appear to diverge from a particular location, without actually being focused there. In other words, when a patient looks into the objective lens 170, a virtual image KI2 of the keratoscope pattern 5 appears to be emanating from the location of the virtual image.

Upon looking into the objective lens 170, the patient's cornea 140 will reflect the perceived virtual image KI2 and create a second virtual image KI3, located approximately 4 mm behind the cornea 140 in the illustrative embodiment. The virtual image KI3 is captured by objective lens 170 and focusing lens 188, which cooperate to create a real image KI4 of the virtual image KI3 on the CCD chip 150.

Figure 2:
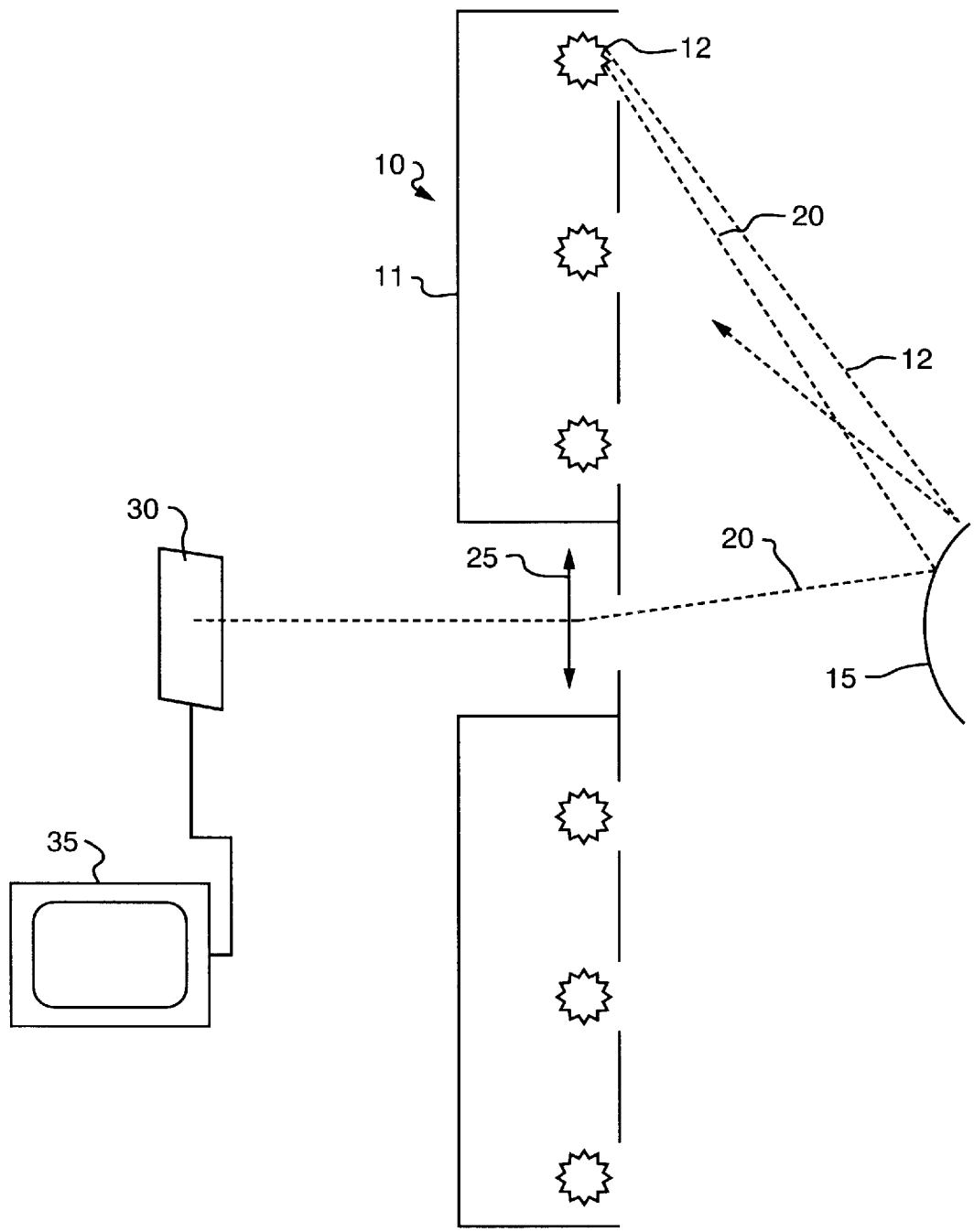
FIG. 2 is a block diagram illustrating the optical arrangement of a prior art topography device.
Figure 3:
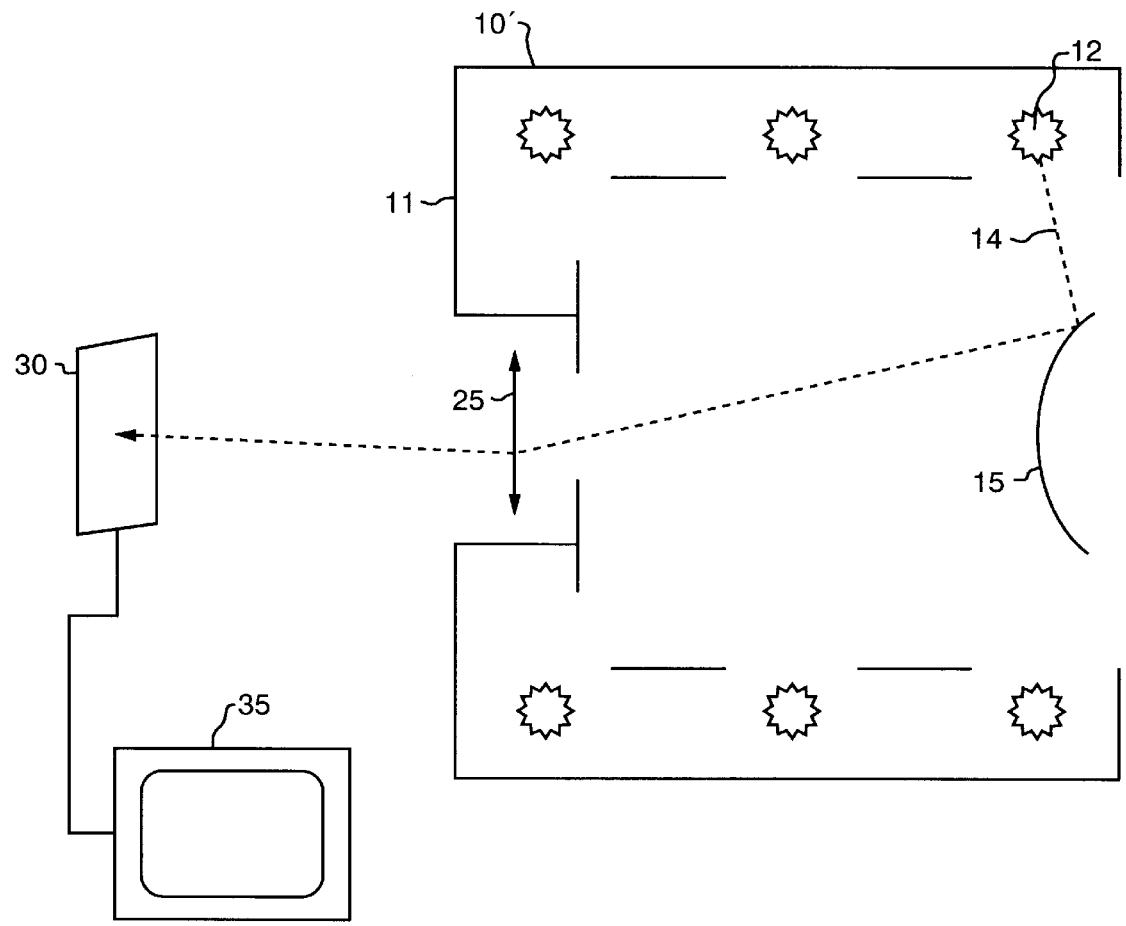
FIG. 3 is a block diagram illustrating the optical arrangement of an alternative prior art topography device design.

Thus, according to a feature of the invention, a virtual image KI2 of the keratoscope pattern 5 is created at a desired distance in front of the patient's eye. Because the distant image is virtual, there is no nose or brow shadow, allowing better coverage of the cornea and providing a design which is relatively insensitive to focusing errors. It has been observed that the accuracy of the present topography system in projecting the keratoscope pattern 5 on the cornea is determined by the apparent location of the virtual keratoscope image KI2, rather than by the actual location of the objective lens 170 in relation to the eye. Thus, the present invention provides a design that is relatively insensitive to focusing, in a similar manner to the prior art design discussed above in conjunction with FIG. 2, as well as exhibiting improved corneal coverage, in a manner similar to the prior art design discussed above in conjunction with FIG. 3.

Figure 6:
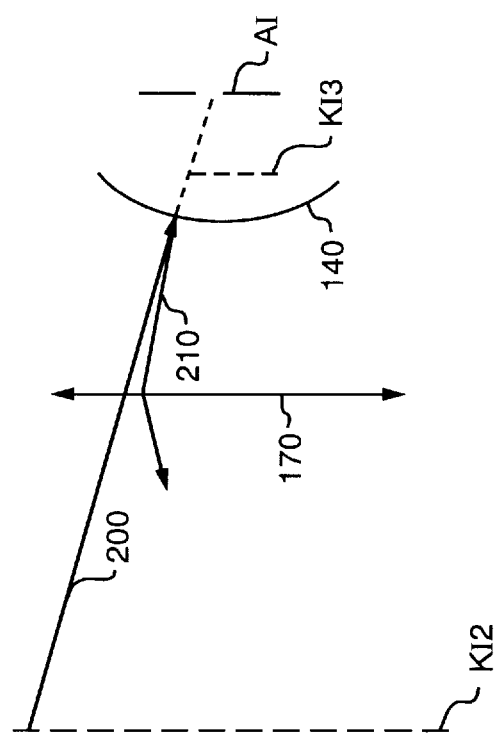
FIG. 6 is an enlarged view of a method of wide angle capture of a virtual image, according to a feature of the present invention.

According to a further feature of the invention, measurement of a large area of the cornea is facilitated by incorporating wide angle capture of the reflected virtual image KI3. As shown in FIG. 6, a light ray 200 from the virtual keratoscope pattern image KI2 travels through the objective lens 170 and strikes the cornea 140 at an angle that is nearly perpendicular to the corneal surface. The light ray 200 is thereafter reflected back from the cornea along a path 210 nearly parallel to the incoming ray 200 from the virtual image KI2 of keratoscope pattern 5. The aperture stop 190 (FIG. 5) is preferably conjugate through the objective lens 170 and focusing lens 188 with a point approximately 7.8 mm behind the corneal surface, corresponding to the center of curvature of a normal cornea, creating a real image AI of the aperture stop 190, approximately at the center of curvature of the cornea, as shown in FIG. 6.

This optical configuration ensures that a ray that reaches the CCD array 150 was reflected nearly back along the incident ray 200, as if emerging from the aperture image AI, thereby allowing a large area of corneal coverage with a target at a significant (virtual) distance from the eye. In other words, this limits reflected rays reaching the CCD chip 150 to those rays that reflect as if they originated at the center of curvature of a normal cornea, creating the wide angle capture that characterizes this system. In this manner, the ray reflected off the cornea 140 can be reflected at a wide angle and still be captured by the large objective lens. In an alternate embodiment (not shown), the aperture stop 190 can be positioned in the optical path between the focusing lens 158 and the objective lens 170, but still conjugate to the center of curvature of a normal cornea through objective lens 170. In this alternate embodiment, the rays emerging from KI2 are directed towards the image AI of the aperture stop 190, so wide angle capture of KI3 is still achieved.

In order to achieve the parameters associated with the illustrative embodiment, namely, so that the center of the aperture stop 190 is approximately conjugate to the center of a typical cornea (having a radius of 7.8 mm), and to place the virtual image at a distance of approximately 0.3 m in front of the cornea with a diameter of approximately 0.4 m, the objective lens 170 should have a diameter of approximately 5.5 cm and an f-number of approximately 0.7. In addition, the objective lens 170 should be positioned approximately 2 cm from the corneal surface.

CENTRATION AND FOCUSING

In order to achieve proper centration and focus of the corneal image, the operator preferably watches a video image of the patient's eye on the computer screen while adjusting the position of the corneal topography device relative to the eye in three dimensions. As shown in FIG. 7, during the centration and focusing operation, the centration illumination source 125 and focusing laser 155 are preferably simultaneously illuminated, while the illumination source 115 is not illuminated. Light rays 240, 245 emitted from the centration illumination source 125 pass through the collimating lens 135 and reflect off beam splitter 180 and beam splitter 165. The rays 240, 245 pass through objective lens 170 and a portion of the rays 240 reflect off the cornea, while another portion of the rays 245 pass through the cornea 140 and are reflected off the patient's iris 142.

The rays 240 reflected off the cornea are captured by objective lens 170, reflect off beam splitter 165, are transmitted by beam splitter 180 and are imaged by CCD chip 150. These rays 240 create an image on the CCD chip 150 of centration illumination source 125 that is reflected from the patient's cornea. Meanwhile, the remaining light rays 245 which pass through the cornea 140 and are reflected off the patient's iris 142, are captured by the objective lens 170, are reflected by beam splitter 165 and imaged onto the CCD chip 150. These rays 245 thereby create an image of the subject's iris 142 and pupil on the CCD chip. Thus, during the centration process a composite image of the patient's iris, pupil and the reflection of illumination source 125 is created on the CCD chip.

The operator observes the composite image on the display and judges the degree of centration of the reflected image of illumination source 125, for example, with respect to a crosshair or other fixed reference mark on the display to ensure that the topography device is in a proper centered position relative to the patient's cornea.

Simultaneously with centration, the focusing laser 155, such as a helium-neon (HeNe) laser, is preferably obliquely illuminating the cornea with a laser beam 247. Most of the laser beam 247 will pass through the nearly transparent cornea, and fall harmlessly against the patient's iris 142. A small percentage of the laser beam 247, however, will be scattered by the cornea. The scattered beam 248 is collected by objective lens 170, is reflected by beam splitter 165 and is imaged onto the CCD chip 150. The operator moves the corneal topography device closer or farther from the patient's cornea to align the image of the scattered beam 248 with the same reference mark used for centration. When the reflection of the centration illumination source 125 and the image of the focusing laser 155 are properly aligned, the operator activates a switch to measure the topography.

In addition, the patient undergoing corneal measurement observes the centration illumination source 125 during the centration process to ensure that the patient's visual axis is aligned with the optical axis of the topography device. In an alternate embodiment, the high intensity centration illumination source 125 emits nonvisible light, so as to be more comfortable for the patient, and light source 115 is simultaneously illuminated to provide a point of fixation for the patient during the measurement.

In alternate embodiments, the centration illumination source 125 can be located at different positions in the optical system 130, as would be apparent to a person of ordinary skill in the art. For example, beam splitter 180 can be positioned in the optical path between keratoscope target 120 and beam splitter 165, with the centration illumination source 125 introduced through the relocated beam splitter 180.

Thus, according to a feature of the present invention, the patient's iris 142 is diffusely illuminated by centration illumination source 125 during centration, thereby allowing easy visibility of the pupil. Further, since the illumination source 115 is not illuminated in the preferred embodiment during the centration process, and thus a keratoscope pattern is not generated, the boundaries of the pupil are not obscured by one or more rings of the reflected keratoscope pattern, as with prior art devices.

TOPOGRAPHICAL MEASUREMENT

Once the operator is satisfied that the composite image has been properly centered and focused on the computer screen, the operator pushes a switch to initiate measurement of the cornea. Upon initiation of the measurement process, the centration illumination source 125 and the focusing laser 155 are turned off, while the illumination source 115 is activated to permit measurement of the cornea. In a preferred embodiment, the personal computer 195 stores at least the last two successive video frames. Thus, at the moment immediately after the illumination source 115 is illuminated, the topography system has one video frame containing the pupil, difflusely illuminated, with no keratoscope image, and one video frame with the keratoscope image reflection with no obscuring detail from the patient's iris 142. From the video frame containing the pupil image, the outlines of the pupil are easily detected. From the video frame containing the keratoscope image, the edges of the keratoscope pattern image are easily detected. The detected keratoscope pattern image is thereafter compared to the stored reference image to yield information about the corneal topography, in a known manner.

CALIBRATION

To calibrate the invention, a calibration sphere (not shown) having a radius of approximately 7.8 mm, to approximate the size of a normal cornea, is positioned, for example, with a bracket that fits the objective lens 170 and holds the calibration sphere at the desired focal point. Calibration proceeds in three steps. First, the operator illuminates illumination source 115 and positions a cursor on the computer screen on the middle of the captured image KI4 of keratoscope pattern 5. Next, centration illumination source 125 is illuminated, and its position is adjusted manually so its reflected image on the computer screen is centered around the cursor. Finally, the image KI4 of the reflection of the keratoscope pattern 5 off the calibration sphere is stored, thereby providing the necessary reference image to calculate the topography of an unknown cornea.

The calibration process involves comparing the known reference radius to the calculated radius for each point on the computer screen. Normally, devices that rely on wide angle optics must contend with significant optical aberrations. The proposed calibration method allows neutralization of aberrations in the system. Each point on the computer screen corresponds to a chief ray emerging in a specific direction from the virtual image of the aperture stop 190 at the center of the calibration sphere. An optical aberration will appear in the calibration sphere image as a deviation of a keratoscope ring, or part of a ring, from the position that would be expected by paraxial optics. When an unknown cornea is imaged, the amount of deviation due to aberrations is unchanged, and can be removed by a subtraction process to yield an aberration-free image from which accurate corneal topography can be calculated.

STRUCTURED LIGHT SOURCE

As previously indicated, the corneal topography system includes a structured light source 110 for creating a keratoscope pattern or another desired pattern. The structured light source 110 preferably includes an illumination source 115 and a beam modulating system 120. The illumination source 115 may be embodied as any light emitting device, including a laser source, a light emitting diode, or an incandescent lamp. The light emitted by illumination source 115, as well as by the centration illumination source 125, is preferably either naturally monochromatic, as in for example light from a laser, or is made monochromatic by the use of a color filter. In this manner, chromatic aberration, which would normally be expected with the use of low f-number lenses, is minimized.

In one embodiment, previously discussed, the beam modulating system 120 is embodied as a piece of photographic slide film consisting of opaque markings on a transparent background, to create the desired pattern. Depending on the application, however, it may be desirable for the beam modulating system 120 to be embodied as a programmable image quality light pattern generator for creating variable patterns. In a preferred embodiment, the programmable light pattern generator 120 is comprised of an array of liquid crystal pixels, capable of selectively blocking incident light in one mode, i.e., by a scattering or absorption process, and transmitting light in another mode, as is well known to those skilled in the art. In this manner, the liquid crystal array can create a desired pattern by selectively placing each individual pixel of the array in a relaxed (light blocking) state, or in an aligned (light transmitting) state, or in an intermediate state between the two extreme positions, according to a "gray scale". The pixels of the liquid crystal array are preferably selectively energized via a driver which may be controlled by the computer 195.

In an alternate embodiment, the structured light source 110 may be embodied as an array of light emitting diodes (LEDs), a cathode ray tube (CRT) or as a laser controlled by an X-Y galvanometer or scanner or any other light generating or transmitting display. In each of these alternate embodiments, an additional illumination source is not required. In a further, less complex, embodiment, variable targets can be achieved, for example, by incorporating a rotatable pattern wheel, with a plurality of selectable positions each creating a unique pattern.

VARIABLE PATTERNS

It has been observed that by modifying the conventional keratoscope pattern, additional or more accurate information can be obtained about the corneal topography. In particular, in order to enhance detection and measurement of nonrotationally symmetric corneas, such as those with astigmatism, a keratoscope pattern which permits identification of the meridian of origin of the reflected ray is preferably utilized. If a particular cornea being evaluated is not rotationally symmetric, angularity will be introduced in the rays reflected from the cornea and the conventional assumption that the target pattern projected through the optical system does not undergo any angular displacement is violated.

Figure 8:
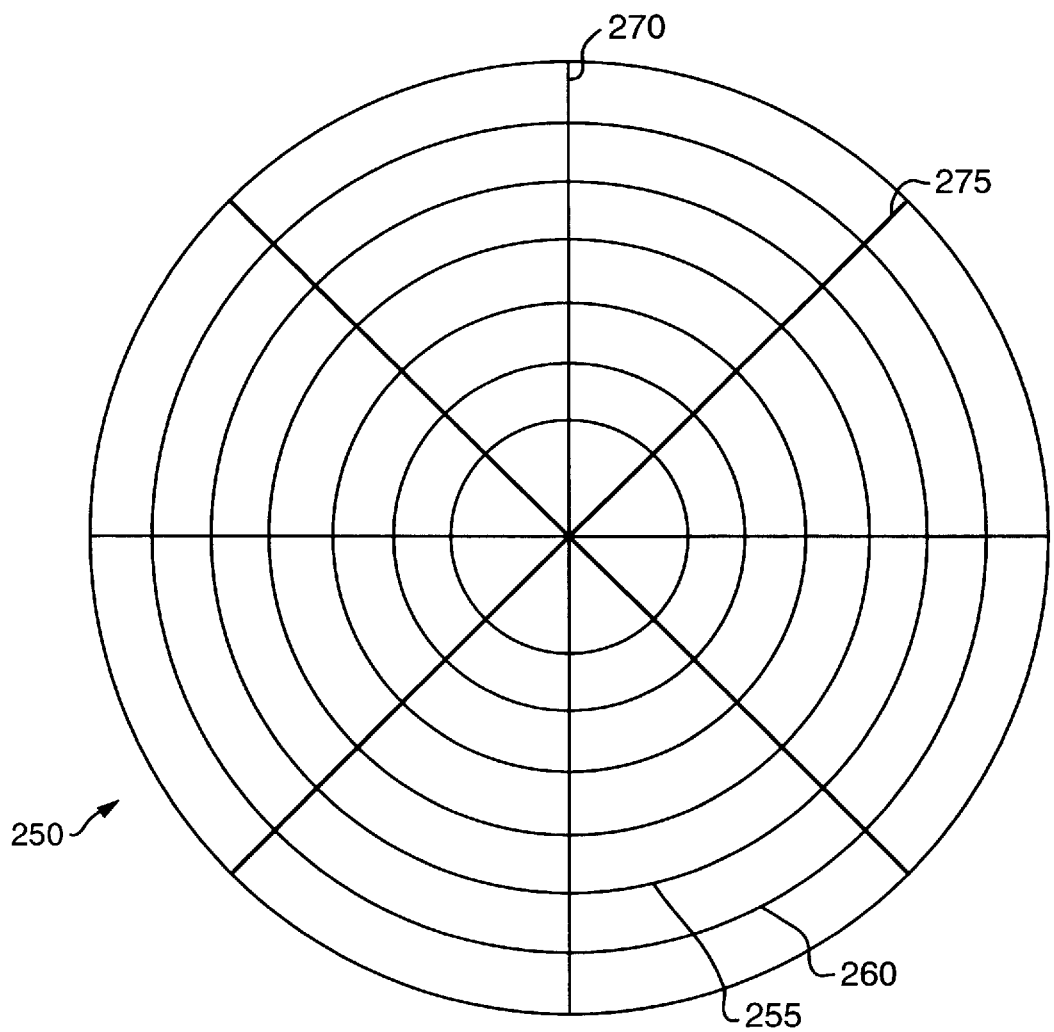
FIG. 8 illustrates an alternative keratoscope pattern for use with the present invention.

Thus, according to a further feature of the invention, an enhanced keratoscope pattern, such as the pattern 250 illustrated in FIG. 8, is utilized. The keratoscope pattern 250 of FIG. 8 consists of a plurality of concentric rings 255, 260 as well as a plurality of radial lines 270, 275. In this manner, when the pattern reflected off the patient's cornea is imaged on the CCD chip, the features on each ring allow identification of rays that leave the plane containing the system's primary axis, and the point of reflection from the cornea. By creating features on the target that differentiate segments of each ring, the problem of non-coplanarity of the prior art is solved. In variations of this embodiment, circumferential marks, a circular or square checkerboard pattern or a grid of perpendicular lines, for example, may be utilized instead of the radial lines 270, 275 to achieve a similar result.

For measurement of abnormal corneas, such as highly curved or unusually flat corneas, it may be desirable to change the diameter or spacing of the concentric rings on the keratoscope target. Thus, it can be seen that when the beam modulating system 120 is embodied as a programmable light pattern generator, such as a liquid crystal array, or as an easily replaceable photographic slide film, in the manner described above, the number of different patterns which can be achieved with the present invention is virtually unlimited. In this manner, the enhanced flexibility in creating patterns provided by the present invention permits greater diagnostic abilities. In addition, the present invention permits the cornea to be initially evaluated with a generic pattern, such as the pattern 5 of FIG. 1, and upon detection of certain anomalies, to be further evaluated with an alternate target which has been designed to optimize evaluation of the particular identified anomaly.

Figure 9:
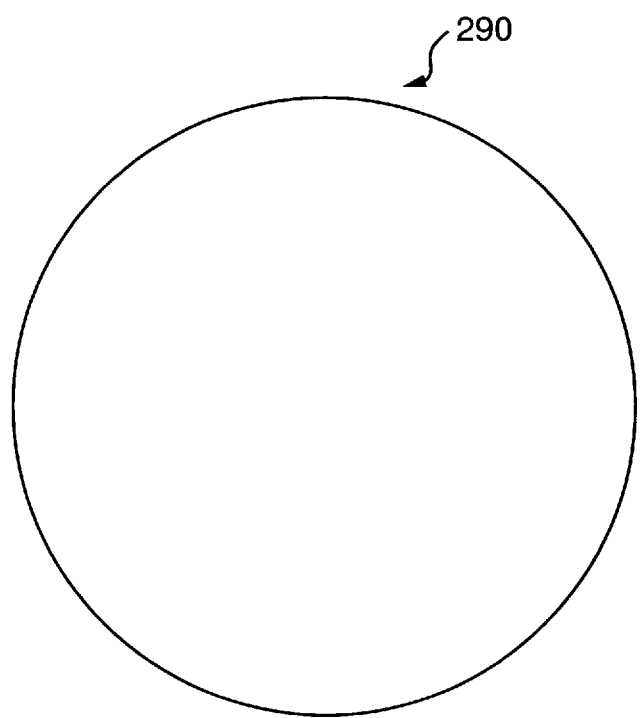
FIG. 9 illustrates a further alternative keratoscope pattern for use with the present invention.

In a further alternate embodiment, a circular pattern 290 may be utilized to allow calculation of corneal curvature in the perpendicular directions in a normal cornea (FIG. 9). This permits the invention to perform ophthalmometry.

PERIMETER

In addition to being useful for evaluating corneal topography, the present invention may also be utilized as a visual field measuring device, or a perimeter. Perimetry is an integral part of general ophthalmic and optometric practice, primarily as an aid to assessing glaucoma, but also to assess maculopathies and optic neuropathies. Typically, the visual field of a patient was evaluated by having the patient view a background, for example, a projection screen or a CRT, that spans a portion of the patient's visual field.

Figure 10:
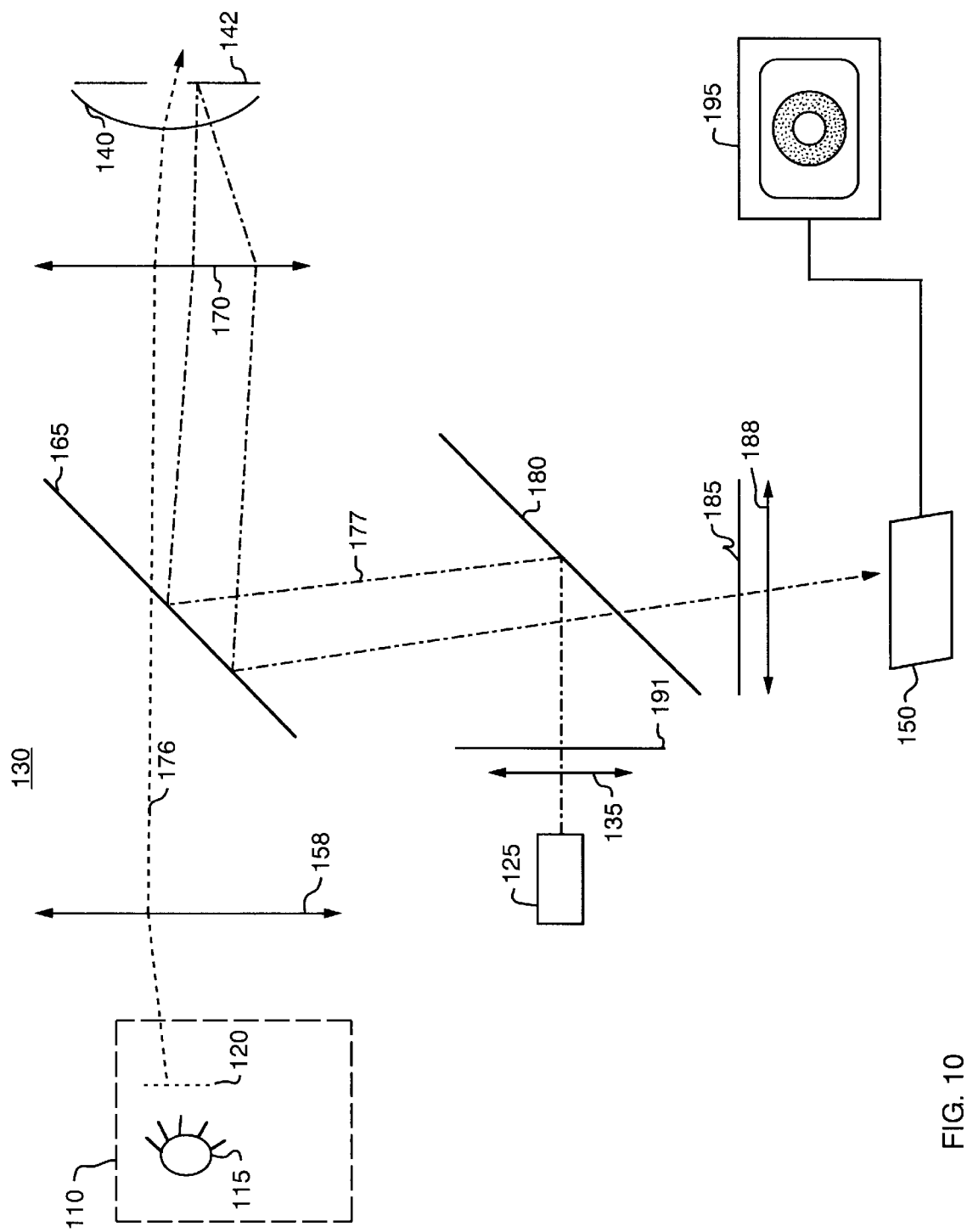
FIG. 10 illustrates the corneal topography device of FIG. 4 reconfigured as a perimeter to measure a patients visual field.

In order to measure a patient's visual field, the optical system of FIG. 4 is preferably reconfigured as shown in FIG. 10. The structured light source 110 is preferably embodied as a liquid crystal display (LCD), a thin film transistor (TFT) LCD display, a CRT or an array of LEDs, to achieve a moving and changeable fixation target, or other active matrix display. As indicated by the light ray 176, the pattern created by the structured light source 110 is captured by focusing lens 158 and directed through beam splitter 165 and objective lens 170. The objective lens 170 creates a virtual image of the pattern produced by the structured light source 110 that is projected at a preferred distance of 1 meter from the patient's cornea, and spans at least 25° of the patient's visual field. During measurement of the patient's visual field, the patient observes the visual stimulus, namely, the virtual image of video display 120, by viewing through objective lens 170.

To measure the patient's visual field, the centration illumination source 125 is preferably embodied as an infrared laser and illuminates the patient's pupil with an infrared beam 177 through a polarizing filter 191 and reflected off the two beam splitters 180, 165. The infrared beam 177 is scattered off the patient's iris, is captured by the objective lens 170, is reflected off beam splitter 165, transmitted through beam splitter 180, through a polarizing filter 185 and focusing lens 188 and imaged upon CCD chip 150, for display on the screen of computer 195. Polarizing filter 185 is oriented perpendicular to polarizing filter 191, so that scattered light from the patient's iris is preferentially transmitted, and reflected light from the cornea is preferentially blocked.

In operation, the device is centered relative to the patient's pupil, by centering the video image of the pupil. The system monitors fixation by tracking the movement of the patient's pupil, using the scattered infrared image. When the center of the pupil image moves beyond a predefined threshold, an alarm may be activated to indicate when fixation is lost. Preferably, the beam modulating system 120 projects a white on gray target of varying size or luminosity to determine threshold sensitivity at each point. Targets of varying luminosity are possible by adjusting the ratio of pixels in the on and off mode that make up each image.

To calculate the position of the pupil in real time, a weighted threshold algorithm is preferably utilized. Initially, the image intensity of all points in the video image is inverted, so that light pixels become dark, and vice versa. This creates a bright pupil on a dark background. Thereafter, all points in the video image with luminance below a predefined threshold are excluded, because they presumably represent iris points. Finally, the unweighted vector center of the remaining points is calculated, representative of the pupillary center.

In an alternate embodiment, the illumination source 125 is aligned with the patient's visual axis so that a bright image of the pupil appears by reflection from the retina of light from illumination source 125. In this case, thresholding can be performed without inverting the pixel intensities, and the unweighted vector center calculated.

It is to be understood that the embodiments and variations shown and described herein are illustrative of the principles of this invention only and that various modifications may be implemented by those skilled in the art without departing from the scope and spirit of the invention.

We claim:

1. An apparatus for evaluating the shape of a cornea, said apparatus comprising:
   a structured light source for generating a diagnostic pattern;
   an imaging system;
   an optical system for projecting a virtual image of said diagnostic pattern to and at a distance in front of said cornea, and capturing a reflection of said virtual image off said cornea, and for redirecting said reflection onto said imaging system; and
   processing means for determining the shape of said cornea by comparing said reflected image detected by said imaging system with stored reference information.

2. The apparatus according to claim 1, wherein said diagnostic pattern is comprised of one or more concentric rings.

3. The apparatus according to claim 2, wherein said diagnostic pattern further comprises means for differentiating segments of said rings.

4. The apparatus according to claim 1, wherein said structured light source is embodied as an illumination source for generating a light beam and a beam modulating system for generating said diagnostic pattern.

5. The apparatus according to claim 4, wherein said beam modulating system is embodied as a liquid crystal array for producing said diagnostic pattern.

6. The apparatus according to claim 4, wherein said beam modulating system is embodied as a programmable light pattern generator capable of producing a plurality of said diagnostic patterns.

7. The apparatus according to claim 4, wherein said illumination source emits non-visible light.

8. The apparatus according to claim 1, wherein said optical system further comprises means for attenuating light scattering off the iris of said eye.

9. The apparatus according to claim 1, further comprising a pupil detection mechanism, wherein said pupil detection mechanism includes an illumination source illuminated independently of said structured light source.

10. The apparatus according to claim 1, wherein the optical system further comprises an aperture stop which is conjugate through the optical system with a point behind the corneal surface, said point corresponding approximately to the center of curvature of a normal cornea, said aperture stop permitting rays of light to reach the imaging system which appear to have originated at said point behind the corneal surface.

11. The apparatus according to claim 1, wherein said optical system includes an objective lens for projecting said virtual image of said diagnostic pattern, said objective lens being positioned approximately 2 cm from the surface of said cornea.

12. The apparatus according to claim 1, wherein rays of light reflected off cornea and captured by the imaging system appear to emanate from a virtual aperture that is behind cornea.

13. The apparatus according to claim 1, wherein said structured light source is essentially monochromatic.

14. A corneal measuring device including a measuring stimulus, an optical system consisting of optical elements, and an imaging device, wherein a virtual image of the measuring stimulus is projected by the optical elements to and at a distance in front of a cornea, wherein light from the virtual image of the measuring stimulus reflects off said cornea and is captured by said imaging device, and wherein the reflected light is analyzed to determine the shape of the cornea.

15. A method for evaluating the shape of a cornea, said method comprising the steps of:
   generating a diagnostic pattern;
   projecting a virtual image of said diagnostic pattern to and at a distance in front of said cornea;
   capturing a reflection of said virtual image off said cornea;
   directing said reflection onto an imaging system; and
   determining the shape of said cornea by comparing said reflected image detected by said imaging system with stored reference information.

16. The method according to claim 15, wherein said step of generating a diagnostic pattern includes the step of generating one or more concentric rings.

17. The method according to claim 16, wherein said step of generating a diagnostic pattern includes generating means for differentiating segments of said rings.

18. The method according to claim 15, further comprising the step of attenuating light scattering off the iris of said eye.

19. The method according to claim 15, further comprising the step of detecting the pupil in said image, wherein said pupil is detected using an illumination source which is illuminated independently of said diagnostic pattern.

20. An apparatus for evaluating the shape of a cornea, said apparatus comprising:
   a monochromatic structured light source for generating a diagnostic pattern;
   an imaging system;
   an optical system for projecting a virtual image of said diagnostic pattern to and at a distance in front of said cornea, and capturing a reflection of said diagnostic pattern off said cornea, and for redirecting said reflection onto said imaging system; and
   processing means for determining the shape of said cornea by comparing said reflected pattern detected by said imaging system with stored information.

21. An apparatus for evaluating the shape of a cornea of a patient's eye, said apparatus comprising:

a structured light source for generating a diagnostic pattern;

an optical system for projecting a virtual image of the diagnostic pattern to and at a distance in front of said cornea, and then for capturing a reflection of said diagnostic pattern off said cornea, and redirecting said reflection onto an imaging system, said optical system including polarizing means for both polarizing the light from said structured light source and attenuating light scattering off the iris of said eye; and processing means for determining the shape of said cornea by comparing said reflected pattern detected by said imaging system with stored information.

\* \* \* \* \*